US00PP10906P

United States Patent [19]

Rampp et al.

[11] Patent Number: Plant 10,906

[45] Date of Patent: May 18, 1999

[54] HYDRANGEA PLANT NAMED 'PARIS RAPA'

[75] Inventors: Franz-Xaver Rampp, Pfaffenhausen; Konrad Rampp, Salgen-Hausne, both of Germany

[73] Assignee: Rampp Jungpflanzen OHG, Germany

[21] Appl. No.: 08/889,779

[22] Filed: Jul. 8, 1997

[51] Int. Cl.[6] ..... A01H 5/00

[52] U.S. Cl. ..... Plt./250

[58] Field of Search ..... Plt./67.1, 250

*Primary Examiner*—Howard J. Locker
*Assistant Examiner*—Melissa L. Kimball
*Attorney, Agent, or Firm*—Webb Ziesenheim Bruening Logsdon Orkin & Hanson, P.C.

[57] ABSTRACT

A new and distinct cultivar of hydrangea named 'Paris Rapa', particularly characterized by intense rose color of the flowers, early growth, storable in the cold and lack of need for chemical growth regulators in the early stage of cultivation and during forcing, particularly suitable for growth in pots, compact and extremely high resistance to mildew.

1 Drawing Sheet

BACKGROUND OF THE NEW PLANT

The present invention comprises a new and distinct cultivar of *Hydrangea macrophylla* known by the varietal name 'Paris Rapa'.

The new cultivar is the product of a planned breeding program which had the objectives of creating a new hydrangea having a compact form and vigorous growth requiring little or no chemical growth regulator and with full and rich bright-colored flowers which survive periods of cool storage, remain on the plant during forcing and require little or no growth regulator.

The new cultivar was selected from a population of seedlings of unknown parentage maintained by Rampp Jungpflanzen OHG, D-8949 Pfaffenhausen, Mindelbergstrasse 7, Postfach 29, Germany. Selection was made by the breeders at Rampp Jungpflanzen OHG in 1994.

Asexual reproduction was accomplished when cuttings were taken from the mother plant and tissue cultured.

The new cultivar has not been observed under all possible environmental conditions. The phenotype may vary with variations in environment such as temperature, light intensity and day length. The following observations, measurements and comparisons describe plants pinched once in autumn and grown in 13 cm. pots in Pfaffenhausen under greenhouse conditions which approximate those generally used in commercial practice.

The following traits have been repeatedly observed and are determined to be basic characteristics of the new cultivar which in combination distinguish this hydrangea as a new and distinct cultivar.

1) Intense rose colored flowers.

2) Early growth.

3) Stroable in the cold.

4) No chemical growth regulators nesessary in the early stage of cultivation nor during forcing.

5) Very suitable for growth in pots.

6) More compact than 'Hermann Dienemann', not patented.

7) Extremely high resistance to mildew.

DESCRIPTION OF THE DRAWING

The accompanying color photographic drawing shows typical flower characteristics of the new cultivar, with colors being as true as possible with illustrations of this type.

DESCRIPTION OF THE NEW PLANT

In the following description, color references are made to The Royal Horticultural Society Colour Chart.

The Plant

Classification:

*Botanic.*—*Hydrangea macrophylla.*

*Commercial.*—Pot hydrangea.

Growth:

*Approximate height of the plant measured from the soil line.*—About 18 cm.

*Outdoor growth requirements.*—The plants are hardy, but only in mild temperate climates. Plants need protection in winter in colder temperate climates, especially when small. The plants prefer indirect light to direct sunlight and windy areas should be avoided.

*Rooting conditions.*—Six weeks of high humidity in a shaded greenhouse. Temperature, especially the substrate temperature, should not be higher than 20 °C.

*Branching after nipping off.*—Two branches grow where a single branch is pinched. Plants are pinched after growth of 2 or 3 pairs of leaves.

*Time of bud formation.*—3 months after the last pinching.

*Suitability for early forcing.*—Depending on the state of maturity, the plants can be forced early. Supplemental light is necessary to force the hydrangeas early. In any case, for early forcing, flower buds should reach a stage of development in which the calyx of the flower is not yet opened, but when the flower is examined under a microscope, individual florets and the petals thereof are distinguishable. Forcing is performed on the plants after winter storage or cold storage at low temperature, preferably at 5° C. under reduced light for at least 6 weeks.

*Time of first flowering.*—The plants can be set up for forcing after 1000 hours at 5°C. Flowering occurs after at least 6 weeks under low light winter conditions. Flowering is sooner later in the year.

*Time of late flowering.*—Plants stored at 5° C. can be forced at any time later in the year if the storage temperature is completely controlled.

*Number of flowers after nipping off.*—Each branch usually has a single terminal flower.

*Habit.*—Compact.

Number of pairs of leaves per branch.—About 4–5.

Flower Stem: Strong, can readily hold the flowers.
Trunk and branches: Woody.
Leaves:
*Arrangement*.—Opposite.
*Surface quality*.—Rough.
*Shape*.—Deltoid.
*Tips*.—Acuminate.
*Bases*.—Obtuse.
*Margins*.—Serrate.
*Size*.—Length: 15 cm. Width: 10 cm.
*Petiole length*:—1.25–2.5 cm.
*Veination*.—Pinnate.
*Underside coloration*.—Light green.
*Color*.—Green Group 137A.

The Flower

Umbel:
*Form*.—Compound, ball-shaped with about 30–50 barren florets and 15–25 fertile florets per umbel. Usually, two barren florets and one fertile floret are present per umbellet, the pedicels of the barren florets are longer than the pedicels of the fertile florets so that the fertile florets are below the barren florerts in the flower.
*Size*.—13 cm in diameter.
Barren flowers:
*Size*.—About 2.5–3.75 cm.
*Number of petals*.—Four.
*Petal Shape*.—Margins are serrated.
*Petal arrangement*.—Two pairs of opposing petals forming a cross-shape.
*Color*.—Upper surface: Red-purple group 57B. Lower surface: Red-purple group 57D. Immature barren florets exhibit a cream-colored throat.
Fertile flowers: Inconspicuous with small calyx having four small green petals and four stamens.
*Fragrance*.—Faintly sweet, if at all.
*Flower bud*.—Globular, about 2–4 mm, develops and opens slowly over two weeks after forcing.

Endurance

Disease resistance: Extremely high resistance to mildew.
Temperature resistance: The plant is for indoor use.
Lasting qualities: This variety lasts much longer than other varieties in this market class. Fertile florets last about 1 week. Barren florets retain their color for about 6–8 weeks and turn green as chlorophyll develops in the petals. The umbels last for month.

We claim:

1. A new and distinct variety of hydrangea plant substantially as shown and described.

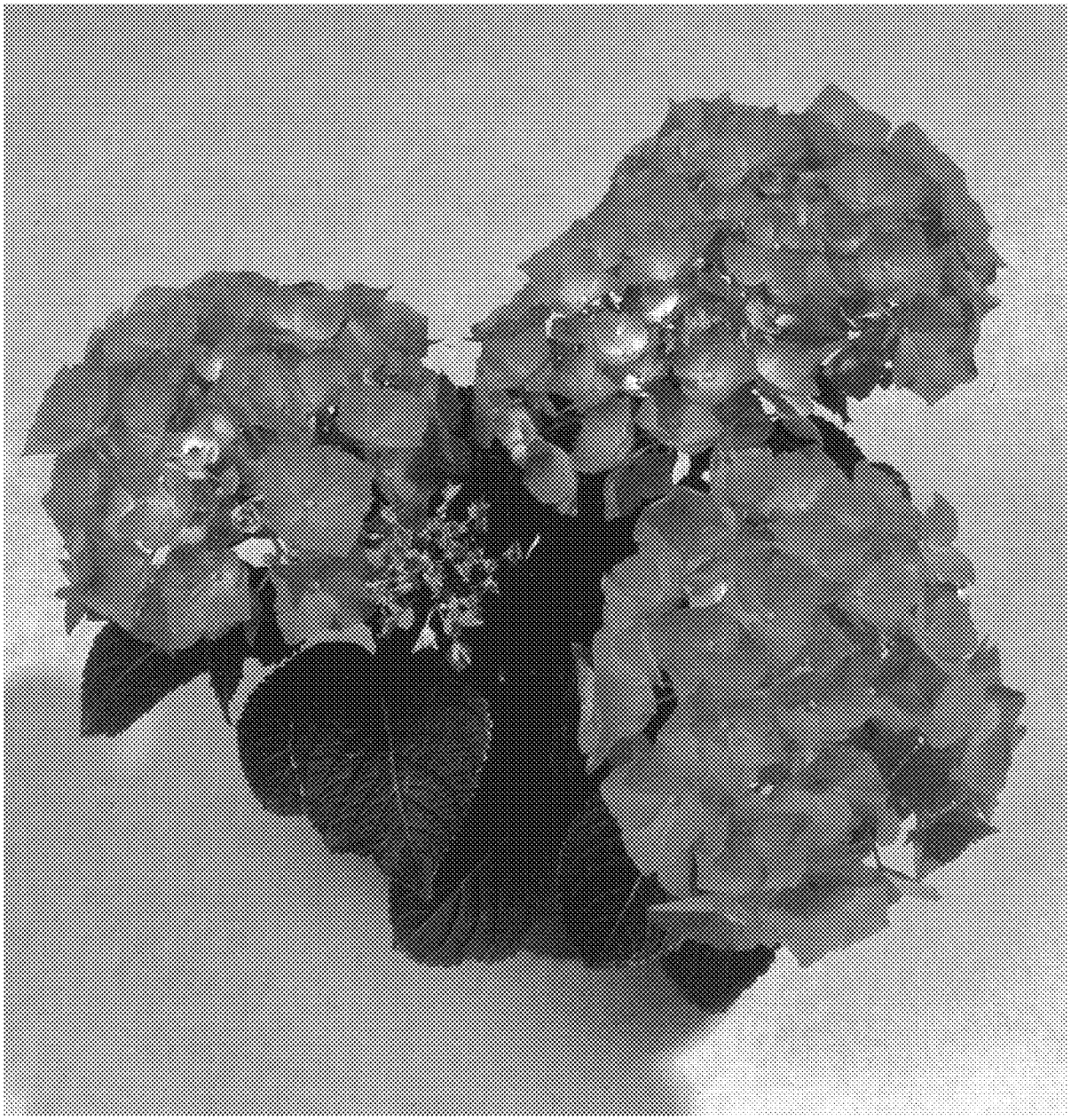

* * * * *